US006197173B1

(12) United States Patent
Kirkpatrick

(10) Patent No.: US 6,197,173 B1
(45) Date of Patent: Mar. 6, 2001

(54) METHODS AND REAGENTS FOR GEL ELECTROPHORESIS

(76) Inventor: Francis H. Kirkpatrick, 37 Clover Hill Dr., Chelmsford, MA (US) 01824

( * ) Notice: Subject to any disclaimer, the term of this patent is extended or adjusted under 35 U.S.C. 154(b) by 0 days.

(21) Appl. No.: 09/344,906

(22) Filed: Jun. 26, 1999

Related U.S. Application Data

(62) Division of application No. 08/746,077, filed on Nov. 6, 1996, now Pat. No. 5,916,427
(60) Provisional application No. 60/006,327, filed on Nov. 8, 1995.

(51) Int. Cl.[7] ..................................................... C08F 2/46
(52) U.S. Cl. ..................... 204/478; 204/470; 204/469; 204/456; 204/466; 204/467; 522/84; 522/86; 522/44; 522/79; 522/33; 522/42; 522/46
(58) Field of Search ................................. 204/469, 456, 204/470, 606, 466, 467, 616, 617, 618, 478; 522/84, 86, 79, 75, 33, 36, 37, 42, 44, 46

(56) References Cited

U.S. PATENT DOCUMENTS

| | | | | |
|---|---|---|---|---|
| 3,914,165 | * | 10/1975 | Gaske | 522/100 |
| 3,925,349 | * | 12/1975 | Gaske | 522/100 |
| 4,017,652 | * | 4/1977 | Gruber | 427/514 |
| 4,246,222 | * | 1/1981 | Monthony | 264/219 |
| 4,323,591 | * | 4/1982 | Wending et al. | 427/53.1 |
| 4,612,336 | * | 9/1986 | Yada et al. | 522/3 |
| 4,704,198 | * | 11/1987 | Ebersole et al. | 204/469 |
| 4,790,919 | * | 12/1988 | Baylor, Jr. | |
| 5,011,762 | * | 4/1991 | Lee et al. | 430/281.1 |
| 5,733,948 | * | 3/1998 | Nelson | 522/79 |
| 5,800,685 | * | 9/1998 | Perrault | 204/291 |
| 5,837,748 | * | 11/1998 | Sorori | 522/26 |
| 5,843,549 | * | 12/1998 | Mingus | 428/40.1 |
| 6,051,367 | * | 4/2000 | Kunita et al. | 430/281.1 |

* cited by examiner

*Primary Examiner*—James J. Seidleck
*Assistant Examiner*—Sanza L. McClendon

(57) ABSTRACT

Polymerization of gels for electrophoresis with improved photoinitiators results in gels which are suitable for electrophoresis. The new initiator systems are much faster than current systems for making such gels. Moreover, the polymerization reaction can be conducted in the presence of oxygen, which greatly simplifies gel casting. In particular, it is possible with the invention to cast and use gels of acrylic monomers in a "submarine" mode, which was not previously possible with acrylamide gels. Continuous casting of gels is facilitated.

19 Claims, No Drawings

METHODS AND REAGENTS FOR GEL ELECTROPHORESIS

PRIORITY

This application is a divisional of U.S. Ser. No. 08/746,077, filed Nov. 6, 1996 now U.S. Pat. No. 5,916,427, which is a continuation-in-part of U.S. Provisional application Ser. No. 60/006,327, filed Nov. 8, 1995.

FIELD OF THE INVENTION

Improved methods and reagents for the manufacture of gel separation matrices for electrophoresis are described, as well as products of the improved methods or with the reagents. The reagents comprise photoinitiators. Gel formats which are novel with ethylenically-unsaturated monomers are described.

BACKGROUND

Gel electrophoresis is an analytical or preparative technique in which molecules are placed in a gel and an electric field is applied. The molecules are typically charged, and move through the gel under the influence of the electric field. In one embodiment, the gel serves only as an anticonvective matrix, and the molecules separate according to their ratio of charge to mass. More typically, the molecules interact with the gel to a significant extent, and larger molecules experience greater steric hindrance due to encountering the gel, and thus move more slowly. In either case, mixtures composed of multiple species of molecule can be separated into the component species, for either analytical or preparative purposes. When the electric field is turned off, the molecules of a given class are found in discrete areas of the gel ("bands" or "spots"), and can be detected and/or extracted as desired.

Gels for electrophoresis made from in-situ polymerized and cross-linked acrylamide are critical materials in life science research and biotechnology. Protein molecular weights are normally evaluated by electrophoresis on polyacrylamide gels in the presence of denaturing detergents, such as "SDS" (sodium dodecyl sulfate), widely cited in scientific articles. Polyacrylamide gels are also used in the separation of small fragments of DNA. In particular, polyacrylamide gels containing urea or other denaturing agents are used for sequencing of DNA, and are one of the technologies which are critical for the human genome sequencing project.

Current widely-used recipes for making polyacrylamide gels consist of the following steps:

1) Make a solution containing an appropriate concentration of an ethylenically-unsaturated polymerizable water-soluble monomer—most commonly, acrylamide, although other such monomers are used in some systems—and also containing a cross-linking agent (most commonly methylenebisacrylamide), and appropriate buffers and optional denaturing agents (such as SDS, urea) for the particular type of gel desired.

2) Prepare the gel cassette for casting. Because the polymerization reaction of the prior art is sensitive to oxygen, the solution to be polymerized must be isolated from the atmosphere during polymerization. In addition, the solution is commonly degassed before polymerization is initiated. Because plastic tends to absorb oxygen, which can be released to the solution during polymerization and cause inhibition of polymerization at the plastic surface, the cassettes for casting polyacrylamide gels are normally made of glass, which is heavy and breakable.

3) Add chemical initiators of polymerization to the gel-forming mixture. In current practice these are usually ammonium persulfate, as a source of free radicals, and TEMED (tramethylethylenediamine), an aliphatic tertiary amine which may function as a carrier of radicals from the peroxygen to the double bonds of the the acrylamide molecules.

4) Quickly pour the activated mixture into the cassette. A small amount of surface area of the cassette, usually one surface (typically the top edge of a slab) or two surfaces (the ends of a capillary) are left open to allow access for the activated mixture, which has begun to polymerize. Well-forming combs are often inserted at this stage. The open surfaces may be overlaid with buffer or other solution, both to achieve flatness and to retard diffusion of oxygen into the surface layer of polymerizing mixture.

5) Wait, typically from 30 minutes to several hours, for the polymerization reaction to be completed. During this prolonged polymerization phase, the fluid pre-polymer mixture may leak from the cassette, thereby requiring repetition of the gel casting operation. The reaction speed can be increased by increasing the concentrations of peroxygen and carrier, but then the working time to cast the polymerizing mixture is significantly reduced.

In the early 1960s, polyacrylamide gels were also polymerized by light ("photopolymerized"), using riboflavin or its more soluble derivative, riboflavin phosphate. However, these gels also required hours to polymerize, were also oxygen-sensitive, and the polymerization reaction was no more reliable than the chemically-polymerized system. Riboflavin-catalyzed systems have fallen into disuse, and citations of riboflavin-polymerized gels in the scientific literature are now only historical.

New photopolymerization systems have since been invented, typically for use in the formation of industrial coatings. The photoinitiator 2,2-dimethoxy-2-phenyl-acetophenone (DMPAP) and related compounds were disclosed by Sandner and Osborn in U.S. Pat. Nos. 3,715,293 and 3,801,329. These patents disclose acetophenones di or tri-substituted at the 2 position, as improvements over acetophenones substituted at the 3, 4 and/or 4' position, analogous xanthophenones, and benzoin and its lower alkyl derivatives. Also disclosed are coatings, including colored coatings, in which a liquid ethylenically-unsaturated material is polymerized to a hard coating using the 2-acetophenones. Osborn and Tercker, U.S. Pat. No. 3,759,807, disclose the combination of phenones, including certain acetophenones, xanthones, fluoroenones, and anthroquinones, in combination with certain amines, for example triethanolamine, for rapid photopolymerization of unsaturated compounds, including acrylamide. Compositions containing no water are of particular interest in all these applications.

The acetophenones operate by a different mechanism than the flavins. DMPAP and relatives, on excitation by an appropriate wavelength of light, photo-dissociate into a pair of radicals. These appear to be highly effective in the polymerization of unsaturated materials. A recent example of their use is given by et al, U.S. Pat. No. 5,410,016, in the synthesis of hydrogels for in-vivo medical applications. Other systems disclosed by Hubbell et. al. as suitable as initiators for photopolymerization in acrylate-derivatized polyethylene glycols include eosin or erythrosin, both derivatives of fluorescein, combined with an amine as transfer agent or co-initiator. The Hubbell and the Osborn patents are hereby incorporated by reference.

Berner and Manse (U.S. Pat. No. 4,609,612) disclose supplementation of benzophenones with benzoylcyclohexanol in photopolymerization. Reilly (U.S. Pat. No. 4,576, 975) discloses carboxylated analogs of "Mitchler's ketone", a diaminobenzophenone, as water-soluble photoinitiators. Moffat et al (U.S. Pat. No. 5.449,724) and Li et al (Macromolecules 28:6692–93, 1995) disclose the use of nitroxides as initiators, although not as photoinitiators.

Various monomers can be used in addition to the conventional acrylamide/ bis-acrylamide solution. It is known in conventional chemically-polymerized gels to use hydroxyethylmethacrylate and other low-molecular weight acrylate-type compounds as monomers; these have been commercialized as "Lone-Ranger" gels. Use of polymers substituted with one or more acrylate-type groups has also been described in the literature (Zewert and Harrington, Electrophoresis 13:824–831, 1992), as especially suitable for separations in mixed solvents of water with miscible organic solvents, such as alcohol or acetone.

In DNA electrophoresis, the most commonly-used gels are made of agarose, a seaweed extract. This material forms a thermoreversible gel on reduction of temperature. Since the reaction is not affected by oxygen, gel cassette design is less constrained, and gels are often cast in plastic containers, and with the upper face exposed to air or buffer ("submarine gels"). However, agarose does not generally have as fine a resolving capacity as acrylamide and many gels for separating nucleic acids, such as DNA sequencing gels, are made by peroxygen-catalyzed polymerization of acrylamide. Since conventionally polymerized acrylamide gels (using peroxygens or riboflavins) cannot be cast in the presence of significant oxygen, the options available for casting techniques are limited. In particular, the "open-face" gels typical of agarose, with 30 to 50% of their surface exposed to oxygen during polymerization (and the rest of the surface area often exposed to plastic), cannot currently be made with ethylenically-unsaturated monomers.

There are other considerations which must be satisfied in casting a gel suitable for the electrophoretic separation of molecules.

First, the gel must have a suitable "format", in that it must be of an appropriate geometrical shape to perform the separation, and it must be placed in a suitable container, or electrophoresis cell, to allow the electric field to be applied, and for excess heat and evolved gas to be removed from the separation area. Gels for electrophoresis are generally either flattened rectangles, cast in a rectangular open box or closed cassette, or are cast as cylinders inside a tube. In current practice, tubes are generally of capillary dimensions (20–200 $\mu$ meter ($\mu$) in inner diameter).

Second, the gel must be generally uniform. Large fluctuations in the local concentration of the gel are clearly undesirable, and can significantly distort a separation (except where deliberately introduced, as in a "step" gradient gel.) A particularly troublesome microvariation is the formation of bubbles during the polymerization; these can sharply degrade performance, especially in capillaries. Local microvariations also degrade performance by causing excessive band broadening during the separation. Such microvariations are thought to arise from heating of the solution during polymerization. Conventional peroxygen polymerization reagents liberate additional heat during the polymerization reaction, further increasing the tendency towards distortions which are inherent in the normally exothermic polymerization of ethylenically unsaturated molecules.

SUMMARY OF THE INVENTION

Novel reagents and methods for the formation of gels for electrophoresis from unsaturated monomers are disclosed, in which the speed and the oxygen-insensitivity of the improved photoinitiation system allows much more rapid preparation of gels, with less likelihood of leaking of the gel-forming solution from the casting device during gel preparation. Moreover, these properties make possible the "open" casting of electrophoresis gels of polyacrylamide and other monomers, and does not require the systematic exclusion of oxygen. The compositions also minimize bubble formation in the casting of gels, especially capillary gels. Likewise, improved compositions for forming electrophoresis gels, and electrophoresis gels formed from such compositions, are disclosed, which allow rapid, oxygen-insensitive photoinitiation and the formation of gels with fewer imperfections.

In particular, the invention comprises an improved composition for the preparation of photopolymerizable gels for electrophoresis, comprising an ethylenically unsaturated monomer, containing on average 1.0 or more units of ethylenic unsaturation; optionally, a crosslinking agent containing on average more than 1.0 units of ethylenic unsaturation; a photoinitiator system, in which the photoinitiator is not a riboflavin; and a solvent, comprising 20% or more, preferably 50 to 90% of the weight of the solution, wherein the solvent is suitable for the electrophoretic separation of at least one mixture of molecular species.

In particular, the photoinitiator is a phenone or a phenone derivative including acetophenones, benzophenones, or anthroquinones, a fluorescein or derivative, a quinone, a radical form of a hindered amine light stabilizer, xanthones, fluoroenones, or other non-riboflavin initiators. Preferably the initiator is an acetophenone di or tri-substituted at the 2 position, an acetophenone substituted at the 3, 4 and/or 4' position, an analogously-substituted xanthophenone, benzoin and its lower alkyl derivatives, fluorescein and derivatives including eosin or erythrosin, and nitroxides. In preferred embodiments, the initiator is 2,2-dimethoxy-2-phenyl acetophenone or eosin Y (tetrabromofluorescein). In preferred compositions, at least 20% by weight of the monomer is selected from acrylamide, HEMA, ethylenically-unsaturated esters or ethers of nonionic polymers, vinylamine compounds including N-vinyl pyrrolidone, and mixtures thereof.

The improved initiation systems of the invention further comprise a nitrogen- or sulfur-containing molecule, preferably a tertiary amine, suitable for improving the efficiency of electron transfer from the photoinitiator to the ethylenically unsaturated monomer.

The invention also comprises methods for preparing a gel for electrophoresis, comprising photopolymerizing a composition suitable for making a gel for electrophoresis in a suitable container, using an initiator of the invention. In particular, the invention comprises a method of preparing a gel suitable for electrophoresis, comprising selecting as the initiator a photoinitiator other than a riboflavin, the photoinitiator being selected to permit the polymerization to a palpable gel of a mixture comprising 10% polyacrylamide and 0.5% methylenebisacrylamide in less than one hour, preferably less than 10 min., more preferably less than about 2 min., at a light intensity, in a wavelength range functionally absorbable by the photoinitiator to permit initiation of polymerization, of 1000 mW/square centimeter, or more typically 100 mW/sq. cm., or even at light intensities suitable for consumer use, such as 30, 10 or 3 mW/sq. cm. A suitable light source for polymerization with some of the photoinitiators of the invention is the UV light box found in many laboratories for the visualization of stained DNA.

In a further aspect, the invention comprises a method of separating molecules, comprising using a gel which has been photopolymerized with a non-riboflavin photoinitiator as a matrix for electrophoresis. Also provided is a gel for the electrophoretic separation of molecules which has been photopolymerized with a non-riboflavin photoinitiator. Likewise provided is a gel made of ethylenically unsaturated monomers, wherein the gel is formed by photopolymerization while having more than 10% of its surface, particularly more than 20% of its surface, and in some embodiments more than 30% or 40% of its surface, exposed to air or oxygen. Similarly provided is a gel made of ethylenically unsaturated monomers, wherein the gel is formed by photopolymerization in the presence of shape-forming constraints which are substantially formed of plastic.

The invention further comprises a method for forming a gradient in a gel suitable for electrophoresis, comprising using as an initiator of gel formation, in a composition capable of forming a gel suitable for electrophoresis, a photoinitiator other than a riboflavin, and imposing a gradient of exposure to light during the polymerization of the gel, the light having a wavelength of about 200 to about 1500 nanometers. Also provided is a gradient gel suitable for electrophoresis, where the gradient is formed by using as an initiator of gel formation, in a composition capable of forming a gel suitable for electrophoresis, a photoinitiator other than a riboflavin, and imposing a gradient of exposure to light during the polymerization of the gel, the light having a wavelength of about 200 to about 1500 nanometers.

DETAILED DESCRIPTION OF THE INVENTION

It has been discovered that with the use of certain initiators it is possible to make gels suitable for the electrophoretic separation of macromolecules by photopolymerization, in a rapid and reliable way that is insensitive to oxygen concentration and requires only the intensity of light sources commonly found in laboratories. The required time of exposure to light is significantly shorter than the time required by prior-art electrophoresis systems. Polymerization in the presence of oxygen also differentiates the invention from the prior art; in particular, it is possible to polymerize a gel of density and uniformity sufficient for electrophoresis in less than ten minutes, even in the presence of oxygen, with the improved reagents and methods of the invention.

In the discussion below, the word "derivative" means the covalent conjugation of the root compound being discussed with relatively small substituents, typically of molecular weight less than about 300 daltons. Thus, acrylate methyl ester, methacrylic acid and crotonic acid are each a methyl derivative of acrylic acid; 2,2-dimethyl-2-phenyl acetophenone is a derivative of acetophenone; etc.

Photoinitiators: A key feature of the invention is a new initiator system for the formation of gels for electrophoresis, comprising a photoinitiator (other than a riboflavin or derivative) and optionally an amine transfer agent, for example triethanolamine (TEOA, or "TO" in the Examples below). This system replaces the currently-favored chemical initiation system for formation of electrophoresis gels, which comprises a peroxygen (typically ammonium persulfate) and an amine transfer agent (usually TEMED, tetraethylmethylene diamine). In this discussion, the term "photoinitiator" includes related materials such as photosensitizers. The photoinitiators are selected from any of several chemical classes, which include acetophenones and benzophenones (collectively, "phenones"), multi-ringed quinones, fluoresceins, azobisnitriles, and derivatives thereof. Suitable initiators include acetophenones di or tri-substituted at the 2 position, acetophenones substituted at the 3, 4 and/or 4' position, analogous benzoquinones and xanthophenones, benzoin and its lower alkyl derivatives, xanthones, fluoroenones, anthroquinones, fluorescein and derivatives including eosin or erythrosin, and nitroxides. Preferred examples of initiators include 2,2-dimethoxy-2-phenyl acetophenone, and eosin Y.

Initiators of the invention, when used as reagents or in methods for making reagents or gels, can be distinguished over prior-art polymerization systems by conferring at least one of the following properties on the improved compositions and methods of the invention, in comparison with the prior art:

1. Rapid polymerization. The time of polymerization can be reduced to below 5 minutes, preferably to below 1 minute, by increasing the intensity of light, while producing gels of a suitable quality.

2. Oxygen insensitivity. The gel can be cast without exclusion of oxygen, as an open system ("submarine" gel) or in the presence of non-degassed plastic. (However, degassing of the gel-forming solution may still be preferred to minimize bubble formation during polymerization.)

3. Decreased formation of bubbles compared to equivalent prior-art systems.

Concentrations: Initiator concentrations may range from less than 1 ppm (parts per million, wt reagent/wt solvent) to over 10,000 ppm. More typical concentrations are in the range of 5 to 1000 ppm. Concentrations of 20 to 200 ppm are usually preferred. The exact optimal concentration will be selected as a trade-off among several factors, including intensity of the available light source (weaker sources require higher initiator concentrations), minimum time required or preferred for the gel-forming polymerization (shorter times require higher initiator concentrations), and possible interaction of the initiator system components with the molecules to be analyzed by electrophoresis (more interaction favors lower initiator concentrations.) Given an initially useful composition, optimization can be achieved for a particular system by routine experimentation. It is customary to optimize a gel system for any novel application, and methods of gel optimization are well known. For example, a description of how to optimize a gel system is found in McDonald et al, BioTechniques 19(3): 464–471, 1995. Some techniques for optimization are described and demonstrated below.

Solvents and solubility: The monomers, crosslinkers, initiators and other reagents must be collectively soluble in a solvent compatible with the separation by electrophoresis of at least one species of molecule. The solvent will comprise, by weight or volume, at least 50% of the composition, typically 70% or more, preferably 80% or more, and often 85% or 90% of the composition. The solvent will usually be predominantly water, typically 80 to 100% water, more typically 90 to 100% water, and usually consisting of water with less than 5% of other solvents, which will usually be electrophoresis-compatible solvents used to solvate photoinitiators or other components of the gel-forming mixture of the invention.

Ancillary Reagents and concentrations: Ancillary reagents include electron transfer agents, stabilizers for the initiator, and specific reagents to support the electrophoretic separation of molecules.

Electron transfer agents include amines and sulfur compounds. Preferred electron transfer reagents are tertiary amines, including TEMED and TEOA (defined above). TEOA is especially preferred. Concentrations of tertiary amine are typically 50 to 2000 ppm (v/v) for TEMED, and 0.01 to 0.5 M for TEOA. TEOA is also a significant component of the buffering capacity of the solution. Many biochemical buffers such as "tris" and Good's buffers contain amine groups, and may be suitable with particular initiators. Suitability of a particular electron transfer agent must be determined in the presence of the particular gel formulation to be polymerized; this is accomplished by routine methods.

Stabilizers include materials which insure that the photoinitiator remains soluble during and after gel casting. With Eosin Y, no additional solubilizers are required. The benzophenones and acetophenones are typically of poor solubility in water, which is the preferred solvent for many electrophoresis separations. Addition of a suitable surfactant or detergent to a concentration of 0.1 to 10%, more typically 0.5 to 3%, will solubilize most photoinitiators of the invention, if solubilization is required. The surfactant must contain a hydrophobic region which can solubilize the photoinitiator, and a hydrophilic region of sufficient extent to create micelles, having a hydrophobic core, which are fully dispersed in water. Most water soluble surfactants will satisfy this criterion. In addition, the surfactant must be compatible with the molecule(s) to be separated, and with the separation procedure. For separation of nucleic acids, a wide variety of surfactants are compatible. These include SDS (sodium dodecyl sulfate), Triton® X-100 (polyoxyethylene nonylphenyl ether), polyoxyethylene-fatty acid esters and ethers ("E8C12"), polyoxyethylene conjugates of fatty-acid derivatized sugars, such as the Tween®, Span® and Brij® surfactants, and water-soluble members of the poloxamer and meroxapol families. In general, non-ionic surfactants are preferred; however, SDS is often acceptable because of its high CMC (critical micelle concentration) and its known compatibility with nucleic acids in some separation procedures. For use in procedures requiring fluorescent detection of the separated molecules, the detergent should have little or no UV light absorption, or fluorescence. This will make detergents with benzene rings (such as Triton X-100) less preferred, and may require purification of detergents to remove such impurities. Methods for doing so are known, and include passage of reagents over activated charcoal or hydrophobic materials such as polystyrene beads.

The final concentration of detergent in the mixture to be polymerized needs to be sufficient to maintain solubility of the photoinitiator. This will vary with surfactant and with photoinitiator, but will typically be about 0.05% to 2.0% (w/v), more typically 0.1 to 0.5%. In DNA sequencing, and in some other types of nucleic acid separations, high concentrations of non-surfactant denaturants (for example, urea, formamide or dimethylformamide) are used. Reduction in final surfactant concentration, or elimination of surfactant, may be possible for gel-forming compositions and formed gels used in these separations. The detergent needed for maintenance of solubility of the photoinitiator may either be added in a stock solution with the initiator, or added separately to the solution. Where practical, combination of the total surfactant requirement with the photoinitiator is preferred for simplicity.

An alternative means of insuring solubility of the initiator, where required, is the inclusion of organic solvents in the gel-forming solution. The solvent must be compatible with the separation to be performed, and is preferably of low toxicity. Preferred solvents include alcohols, such as methyl, ethyl, isopropyl, and tert-butyl alcohols; acetone; DMSO (dimethyl sulfoxide); glycols and esterified glycols (such as propylene glycol, or its lower-alkyl ethers); dimethylformamide; formamide; and pyrrolidone. Such solvents are preferably water-miscible, to at least the extent required for photoinitiator stabilization. Combinations of solvents, denaturants and surfactants are also effective in solubilizing the photoinitiator where required.

For proteins, surfactant choice is strongly influenced by the type of separation and the nature of the protein. The most common procedure for electrophoretic separation of proteins is "SDS-PAGE", i.e., electrophoresis in polyacrylamide gel in the presence of sufficient SDS to denature the proteins. Typical final SDS concentrations in the electrophoresis gel are in the range of 0.01% to 1.0% (w/v), but may be zero. The other common protein separation procedure in electrophoresis is the separation of blood proteins. This procedure is subject to shifts in protein mobility if surfactants are used. Use of photoinitiators not requiring detergents for solubilization—such as Eosin Y—is preferred for such separations.

Other surfactants can be used in the stabilization of the photoinitiation system provided that they do not interfere with the separation or with the polymerization of the electrophoresis gel. Over a hundred surfactants are available commercially, for example, in the Sigma catalog. Determination of the suitability of a surfactant in a particular separation is readily determined, for example by including the surfactant in a prior-art gel formulation, and observing any change in separation properties.

Light Sources: The light source should emit sufficiently in the absorption band of the photoinitiator to initiate the polymerization in a short period, typically a few minutes. Any light source emitting in the UV, visible, or infrared is suitable with the appropriate initiator. Preferred frequencies are the near-UV (UV-B; long-wave UV; ca. 330–400 nm), especially for acetophenone initiators, and the blue to green (450–550 nm) for eosin Y. Any type of emitter with sufficient energy is suitable, including fluorescent lamps, incandescent lamps, arc lamps, lasers and photoemitting diodes. There is no requirement for monochromicity or parallelism of the beam. It is preferable for the source to have reasonable uniformity in its emissions over the area of the gel being polymerized. This is conveniently achieved by use of diffusers. Preferred sources, because of their ready availability, include UV light boxes used for detection of DNA in gels, and inexpensive sources such as hand-held UV lights (e.g., Fisher Scientific catalog).

Gel-forming monomers: Any substantially-water-soluble molecule containing a photopolymerizable reactive group, in combination with a material which can form cross-links, is suitable for formation of gels for electrophoresis by the methods of the invention, provided that the combination, once polymerized, forms a gel suitable for the particular type of electrophoresis. Exemplary materials include acrylamide, in combination with methylene-bis-acrylamide or other known crosslinkers; hydroyethylmethacrylate and other low-molecular weight (less than about 300 daltons) derivatives of acrylic acid, methacrylic acid, and alkyl-substituted derivatives thereof, such as crotonic acid; vinyl pyrrolidone and other low-molecular weight vinyl and allyl compounds; vinylic, allylic, acrylic and methacrylic derivatives of nonionic polymers, including such derivatives of agarose ("Acrylaide" crosslinker, FMC Corp.), dextran, and other polysaccharides and derivatives, such as cellulose derivatives including hydroxyethyl cellulose; polyvinyl alcohol; monomeric, oligomeric and polymeric derivatives of glycols, including polymers of ethylene oxide, propylene oxide, butylene oxide, and copolymers thereof; acryl, vinyl or allyl derivatives of other water-compatible polymers, such as polyHEMA (polyhydroxyethyl acrylic acid), polymeric N-isopropyl acrylamide (which is temperature-sensitive), maleic-acid polymers and copolymers, partially hydrolysed EVAC (polymer of ethylene with vinyl acetate), ethyleneimine, polyaminoacids, polynucleotides, and copolymers of the subunits of these with each other and with more hydrophobic compounds such as pyridine, pyrrolidone, oxazolidine, styrene, and hydroxyacids. Non-ionic compounds are preferred; acrylamide is especially preferred. The polymerizable materials need not be entirely water-soluble, especially when solvents or surfactants are included in the gel-forming solution. Methods for making polymerizable derivatives of common polymers are known in the art; for example, addition of allyl glycidyl ether to hydroxyl groups is known, as is esterification of hydroxyls with acids, anhydrides or acyl chlorides, such as acrylic anhydride. Amines are readily derivatized with acyl anhydrides or chlorides.

Many of the derivatized polymers described above will contain more than one reactive group, and so are self-crosslinking. Addition of a crosslinking agent, which contains on average more than one reactive group per molecule, is required for formation of gels from monomers which have only one reactive group, such as acrylamide. These include, in addition to multiply-derivatized polymers, methylene bis-acrylamide, ethylene glycol diacrylate, and other small molecules with more than one ethylenically-unsaturated functionality, such as acryl, vinyl or allyl.

Gel Formats:

The reagents for forming gels of the invention may be formed into any convenient shape, provided that the shape is suitable for an electrophoresis separation, and is sufficiently reproducible to allow accurate analysis or purification. Such gels may be cast within classical cassettes, which generally consist of two plates of glass, separated by spacers, and blocked at a lower edge by a temporary fluid-retaining means to retain the polymerization mixture in the cassette until gelled. Examples of such cassettes are in common use for the separation of proteins and of carbohydrates, and in the sequencing of nucleic acids. Other formats include capillaries, in which the gel-forming mixture is introduced by capillary action or by a pump, and is retained in the capillary during polymerization by capillary action or by the blocking of one end. A third significant form is the open-cast gel, which has until now only been achievable with polymers gelling by thermal or ionic means. These are most commonly used either as "submarine" gels, for separation of nucleic acids, or as thin gels with a planar surface exposed to air, normally supported on a planar plastic support, for the separation of clinically-significant proteins, such as those of serum or cerebrospinal fluid.

Because of the enhanced controllability of the gel-forming reagents of the invention, free-radical polymerized gels can be made in formats not previously practical. One example, noted above, is the creation of "submarine"-type gels from polymerizable ethylenically-unsaturated monomers; such gels could only be made from thermogelling monomers, such as agarose, in the prior art. As another example, it is currently tedious to make "gradient" gels by any method. In a gradient gel, the density, either of concentration or of crosslinking or both, of the separation matrix varies systematically through the length of the gel (or in some cases, the width), usually from a lower density at the point of sample application to a higher density at the distal end of the gel. In a rapidly-photopolymerized gel, a gradient of final polymer concentration or crosslink density can be created in the gel by use of a variable-density optical filter, or "wedge", which absorbs light differently in different regions. By use of an optical wedge, a polymer gradient can be created even in a uniform and unconstrained gel, such as a submarine-style gel. Thus, when the presence of un-polymerized monomer and/or crosslinker is acceptable in the electrophoretic separation, it is as easy to make a gradient gel, with the present invention, as it is to make a linear, non-gradient gel. It is further possible to make a gradient gel in formats in which such a gel was not practically possible, such as in open-cast horizontal formats including submarine gels and clinical gels.

A particularly attractive use for the improvement in separation possible for such gels is the DNA sequencing gel, where the number of bases readable in a lane can be increased by using a gradient. Moreover, a sequencing gel can easily be cast in an open horizontal configuration with the new reagents, optionally with a gradient This enables mass production of such gels, which can be supported on a polymer film as described in the literature. Application of a gel-forming mixture of the invention onto a belt, or a moving roll of polymer film, with thickness controlled either by the means of deposition, such as a transfer roll, and/or by positive thickness control after deposition, for example by a "doctor blade" (levelling edge), followed by controlled illumination, optionally through a mask to impose a gradient, will produce a uniform or gradient gel. Using the reagents of the invention, such a process can be simpler and faster than analogous procedures described in the art, for example by Fuji Photo Film. Because exclusion of oxygen is not required, such processes can also be more efficient.

Given an initially functional gel recipe, it is known how to optimize that recipe for best performance in a particular separation. Certain information for such optimization is best acquired in preliminary experiments; other information is best obtained on examples of actual gel-forming (pre-production) mixtures. Reference has been made to literature techniques for the optimization of gels. In the illustrations below, methods of selecting conditions for gel formation using the methods and reagents of the invention are described. These are intended to be illustrative, rather than exhaustive; alternative techniques for practice of the invention or evaluation of reagents are readily accessible to those skilled in the art. By use of these methods, or alternatives, practitioners can readily optimize the use of photoinitiator systems of the invention for their particular applications of electrophoresis, without undue experimentation.

1: Time to Polymerize in Test Tubes.

A standard acrylamide/bis-acrylamide ("bis") monomer mixture is prepared essentially according to Laemmli (described in Sambrook et al, Molecular Cloning, Cold Spring Harbor Press; p. 18.47 ff.), at a ratio of acrylamide to bis of 19:1 and a final total monomer concentration of 8%, in standard TBE buffer ("tris"/borate/EDTA, 89/89/1 mM, pH about 8.4) About 2 ml of monomer mixture is dispensed into test tubes, and initiators are added. Gelation is determined by tilting the test tube and observing whether the meniscus moves or not. A gel detected by either method, or by any other method that relies on the physical coherence of the gel, may be called a "palpable" gel. In certain samples where the meniscus does not gel, but the solution lower in the test tube does gel, the test above is supplemented by insertion of a toothpick into the mixture before gelation. Lack of movement of the toothpick upon tilting of the test tube indicates gelation. In the standard mixtures of Laemmli, when using a light source of at least 10% of the intensity of the usual UV box for visualization of ethidium bromide-stained DNA, mixtures containing either DMPAP or eosin, at some concentration between about 20 to 1000 ppm, and at least 100 ppm of TEMED or TEOA, will polymerize. The exact concentration of initiator can then be chosen based on a tradeoff between minimization of initiator concentration, and adequate speed of polymerization for the light source available.

2: Test Polymerization of Gels in Submarine Mode.

Using the preliminary conditions of the previous experiment, a submarine electrophoretic gel casting solution is made by preparation of a mixture containing reagents according to Laemmli with the replacement of the APS with the appropriate amount of initiator. The mixture is poured into the casting tray of a conventional submarine mini-gel electrophoresis cell, and is then polymerized by application of light for a suitable time determined from the previous experiment, such as 10 minutes, to ensure complete polymerization. After the solution gels, the comb is removed, and samples of molecular weight standards of either DNA or protein are placed in the wells. Electrophoresis is conducted under conventional conditions, and resolution of the samples is obtained.

It is thus verified that "submarine" gels can be cast with conventional reagents, such as acrylamide, if the novel initiators and processes of the invention are used. This is not possible with prior-art acrylate-based acrylamide gels. Once efficacy is affirmed, then the initiator concentration is systematically reduced from the starting level, or the time of exposure is systematically reduced, until the polymerization time is in a desirable range, typically one minute or less, and the initiator concentration is a low as possible.

3. Non-acrylamide Monomers.

Because of the higher effectiveness of the inventive systems in the presence of oxygen, compared to the conventional systems (peroxides or riboflavins as initiators), virtually any ethylenically-unsaturated compound is potentially of use in the invention, provided that its other properties are compatible with the formation of electrophoresis gels and the separation of samples by electrophoresis. These include the monomers listed above, and others with similar characteristics. To determine the suitability of a given monomer and/or crosslinker in formulations of the invention, trial gel mixtures are made, and polymerized initially with the concentrations of initiator and of other reagents determined as described above. After determining both the time to polymerize, and the electrophoresis properties of the gel, such as relative migration distance of molecules compared to standards (Rf), the concentration of initiator can be optimized for the particular monomer system. Not all combinations of monomers and crosslinkers will be suitable for electrophoresis, but suitable compositions are easily determined, validated and optimized in such experiments. Candidate monomers and/or crosslinkers not currently in wide use in electrophoresis include allyl alcohol, HEMA (hydroxyethyl(meth)acrylate), polyethylene glycol monoacrylate, polyethylene glycol diacrylate, ethylene glycol monoacrylate, ethylene glycol diacrylate, vinylcaprolactam, vinylpyrrolidone, allylglycidyl dextran, allylglycidyl derivatives of polyvinylalcohol and of cellulose and derivatives, vinyl acetate, and other molecules containing one or more acryl, vinyl or allyl groups.

The molecules for polymerization must be soluble in the solvent system used for electrophoresis of the particular molecule to be analysed, to a sufficient extent to provide the required sieving power. For example, acrylamide gels normally contain 5% to 20% by weight of acrylamide, and the monomer must be soluble to at least that extent in the solvent used. The solvent is normally water, but may also contain surfactants, or water-miscible organic solvents; it is the limiting solubility or dispersibility of the ethylenically-unsaturated monomer in the actual solvent and surfactant mixture used to form the gel that is important. Thus, with appropriate amounts of organic solvents, such as alcohols, and/or with the addition of surfactants, monomers such as vinylpyridine or styrene may also be found to be of use in electrophoresis using the methods of the invention. Thus, the use of the compositions and methods of the invention allows a wide range of unsaturated monomers to be used in the formation of gels for electrophoresis.

4. Photoinitiators.

A variety of photoinitiators and photosensitizers (collectively referred to as "photoinitiators" herein) are suitable for the present invention. Photoinitiators have the ability to initiate a free-radical, cationic or anionic polymerization reaction in a solution containing ethylenically-unsaturated monomers under the influence of light. The wavelength of the light is most commonly UV-A, UV-B, or visible, but may range from far UV (200 nm wavelength) to near infrared (1500 nm). Photosensitizers are sometimes distinguished from photoinitiators by requiring the presence of an auxiliary agent, such as an amine, to transfer electronic excitation from the photosensitizer to the ethylenically-unsaturated compound. Such agents are known optional ingredients for use in conjunction with photoinitiators, to make the reaction more efficient. All of these systems are referred to as "photoinitiators" in description of the present invention.

Photoinitiators are tested for suitability in the invention as follows:

A). A composition known to be suitable for the preparation of a gel useful in electrophoresis is prepared, excluding an initiation system. For example, a mixture of monomers, crosslinkers, buffers and denaturants (if required) would be prepared as an aqueous solution at appropriate compositions of the various ingredients. The concentrations will typically be somewhat higher than those desired in the final post-polymerization gel, to allow a volume of initiator to be tested to be added. Typically, 5 to 10% of the final volume will be reserved for the initiator solution, although the volume in which the initiator is added may range from about 50% to less than 0.01% of the final solution volume.

B). The initiator to be tested is added at a range of concentrations to the gel-forming solution. Final concentrations of the initiator in the gel-forming solution may range from less than 1 ppm (parts per million) to more than 10,000 ppm. Varying concentrations by factors of about 3 is an efficient method for initial evaluation (e.g., 1, 3, 10, 30, 100, 300, 1000, 3000, 10,000 ppm). If the initiator is not sufficiently soluble in water to prepare a stock solution, where the initiator stock solution will be diluted by a factor of 2 or more in the preparation of the final solution for polymerization, then a suitable surfactant or organic solvent will be used to solubilize the initiator. (Surfactant selection was discussed above.)

C). The test initiator solutions, preferably accompanied by a negative control (no initiator) and a positive control (an initiator known to work), are exposed to light of an appropriate wavelength and intensity and for a known amount of time. The time may be variable, in that exposure to the light is continued until the solution gels, or up to an upper exposure time, and the time of gelation is recorded. Test solutions are evaluated for gelation. Based on these results, optimal concentrations of an initiator can be chosen, if the initiator is actually effective.

5. Transfer Agents Accelerators and Co-initiators.

Improvement of polymerization efficiency can be achieved by addition of transfer agents, accelerators, co-initiators and the like. Selection of such agents may be achieved by finding a suitable concentration of photoinitiator, along with a suitable light intensity, wavelength, and time of exposure, as outlined above. Experiments are conducted as described in the preceding section.

OPERATIONAL EXAMPLES

Example 1
Selection of Initiator Concentration.

Reagents were of standard commercial grade and used without further treatment. Solutions were prepared to contain (final concentrations) 10% w/v acrylamide/bisacrylamide, 29:1; 0.09 M triethanolamine ("TO") buffer, pH about 8; and variable concentrations of dimethoxyphenylacetophenone ("DMP") ranging from approximately 1600 parts per million (ppm; wt/vol) down to about 2 ppm; and 0.5% wt/vol sodium dodecylsulfate ("SDS"). The DMP was taken up in ethanol and diluted with 0.5% SDS to form a 5000 ppm stock solution (as a colloidal suspension), which was further diluted in 3-fold dilutions to obtain a series of working dilutions.

Aliquots of 1 ml of each dilution were placed in small test tubes and exposed to a long-wave UV ("UV-B") light source, a hand-held model UVL-56 Blak-Ray® lamp made by UVP of Upland, Calif. and obtained from Fisher Scientific. The peak intensity is stated to be near 366 nm.

In exposures of 10 seconds, followed by examination of each tube for gel formation by tilting the tube, the three most concentrated mixtures (5000 ppm stock or 2500 ppm final, and the ⅓ ("830 ppm final") and ⅑ ("275 ppm final") dilutions of this) gelled in about 30–50 sec., 70–80 sec., and 120–150 sec., respectively. Lower concentrations did not gel in 15 minutes. Controls not exposed to the lamp also did not gel.

Example 2
Emulation of Submarine Gel.

At the 500 ppm final level, 30 ml of solution was prepared as in Example 1 and poured into a rectangular plastic box (the lid of a pipet tip rack). The lamp was placed on top of the box and turned on. After 2 minutes, gelation had begun. At 5 min., there was a layer of gel on the entire bottom of the solution, and a thin layer of fluid on top. The solution was almost entirely gelled at 7 minutes. The gel was rinsed and its texture was evaluated by hand. It felt comparable to a standard 10% acrylamide gel prepared by standard methods.

Examples 1 and 2 demonstrate that it is straightforward to find operative conditions for the production of gels of the invention.

Example 3
Photoinitiation with Eosin Y.

A commercial 5% solution of Eosin Y was serially diluted in the TO buffer of Example 1 and mixed 1:1 with a 20% stock of acrylamide/bis in TO. Final eosin concentrations ranged from 25,000 ppm (2.5%) down to about 0.4 ppm. Solutions were tested with both the long-wave UV light, and with a green light. The green light was a "Unilamp" obtained from Midwest Scientific Co., Mission, Kans.; it is believed to select green light from a fluorescent-type bulb, and was designed for inspection of optical components for flatness. Eosin is known to absorb in the green and fluoresce.

In the UV, an optimum concentration of eosin was observed. Concentrations of 11 to 34 ppm gelled in less than 1 min., and concentrations of 100 to 900 ppm partially gelled in 1 min., and completed gelation on further standing, with or without continued exposure to UV. Green was ineffective with these solutions. Concentrations of 2500 ppm or above, or 4 ppm or below, did not gel even with UV for 5 min. or more.

Thus, the range of 34 to 103 ppm was approximately optimal.

Example 4
Effects of Buffer Substitution and Electron Transfer Agent.

The TO buffer of examples 1 and 3 was replaced with standard "TBE" electrophoresis buffer, prepared from a commercial powder blend. TBE is about 0.09 M in "Tris" (trishydroxyethylaminomethane) and in borate, and contains about 2 mM EDTA. At 100 ppm of eosin, no gelation was observed out to 10 minutes in the UV. However, if the electron carrier TEMED was added at 2000 ppm, then gelation occurred in 2 to 3 minutes.

Example 5
Preparation and Electrophoresis of a Submarine Gel.

50 ml of a solution containing 8% acrylamide/bis, 1×TBE (90 mM), 2 microliter TEMED and 2 microliter 5% Eosin per ml solution) was prepared and poured into the casting chamber of a standard submarine mini-gel apparatus, and a well-forming comb was inserted. The solution was illuminated in the long-wave UV for about 5 min. to obtain a solid gel. The gel was placed in an electrophoresis cell, submerged in 1×TBE, and DNA molecular weight standards in bromphenol blue dye were loaded into the wells.

On application of voltage with the correct polarity, the bromphenol blue migrated as spots in the gel as expected. However, the DNA was not detected after staining with ethidium bromide, probably due to interference by residual eosin.

Example 6
Comparison of Photoinitiators with Various Additives and Light.

Using reagents as in previous examples, but with DMPAP dissolved in ethanol at 0.5% (5000 ppm), the polymerization of Ac/Bis was compared at 100 ppm photoinitiator in eosin vs DMPAP, each at 100 ppm (green) or at 20 ppm (Eosin) vs 100 ppm (DMPAP) in UV; in triethanolamine/HCl vs Tris/Borate/EDTA buffer; with and without TEMED; and in polymerization with near-UV vs green light, although without control for light intensity. The following results were obtained:

1. In UV light, at about 5 min. no tubes had polymerized, but at 6 min., ½ of the tubes had polymerized with DMPAP in TO±TEMED, and in TBE+TEMED. By 12 min., at least 50% of all conditions had polymerized except for DMPAP in TBE±TEMED.

2. In green light, no DMPAP test polymerized, as expected. Eosin with TO±TEMED polymerized at 15 to 20 min, and Eosin in TBE with TEMED (but not without) polymerized by 20 min.

These experiments, performed in about 4 hours, demonstrate the ease of comparative selection of conditions for forming photopolymerizable gel compositions.

Example 7
Polymerization of PEG-diAc.

Solutions were made which contained 10% (V/V) of PEGdiAc (polyethyleneglycol-400-diacrylate, from Aldrich Chemical) and buffers and initiators as above. TEMED concentrations were only 0.5 microliter/ml, 500 ppm, about 25% of the previous concentration.

Under similar conditions as above, it was found that no mixture polymerized after 5' of alternate side and top illumination (1 min. each) with UV. At 6 min, the front (but not back) of each pair, i.e., the tube closer to the side illumination, polymerized under P/TO±D conditions, i.e., with DMPAP at 100 ppm in TO buffer with or without TEMED. At 10 min., both members of the P/TO pairs were polymerized, and the front member of the PB/PBD pairs had gelled. At 12 min., no further samples had gelled.

Ammonium persulfate was added to the "back" member of all Eosin samples after 12 min. of UV light exposure. At 15 min, the E/TO and E/TO/TEMED samples had gelled. The other members of each pair had not gelled in the UV.

The green light source was used on the residual ("front") E samples, and APS was added to the non-gelled P samples, which were removed from light exposure. After about 4 min., the E/TO samples had gelled in the green light. The gels were less turbid than the UV-gelled or the APS-gelled samples. An additional 7 min. of green exposure produced no significant changes.

Formed gels were scraped out of the test tubes and their mechanical properties were qualitatively evaluated by hand. The PEGdiAc gels polymerized by UV or by APS were white, crumbly, and "dry" to the touch, even though of similar water content to other gels. The eosin-polymerized aPS gels were more like the Ac/Bis "PAG" gels made in previous experiments.

Since it has been reported in the literature by Harrington that gels suitable for electrophoresis can be made from PEGdiAc monomers, clearly the PEG formula can be adjusted to give gels of the appropriate physical consistency.

What this experiment with PEGdiAc demonstrates is that:
1. Gelation in a reasonable time can be achieved on the first trial of extrapolation to a new monomer system. Thus, only a reasonable amount of experimentation is required to extend a known set of results to a new area.
2. The general pattern observed with AcBis gels holds with PEGdiAc gels, with minor variations: TEMED has little effect; eosin is effective in green, DMPAP in near UV, as expected; at low TEMED concentrations, TO buffers are much more effective in polymerization than TBE buffers.

Example 8

Preparation and Use of Slab Gels for Electrophoresis.

Submarine-style gels were made from 40 ml of 10% ac/bis in 1% TBE with 0.1% SDS and 200 microliters each of TEMED and Eosin stock in 50 ml. The casting tray was placed on top of the active surface of the green light source (which was bigger than the tray), and the source was in turn balanced on the horizontal electrophoresis tray for levelling. This setup anticipates the expected "end customer" use of the invention, by using a UV or visible "light box" for polymerization of such gels.

Under green illumination, polymerization was complete in about 10 min.

After 10 min. pre-electrophoresis, protein samples were applied (Sigma wide-range protein standards, cat. no. M-4038) in amounts varying from 1 to 8 microliters in the eight wells. Electrophoresis was begun at 150 volts, giving about 80 mA. The dye front moved into the gel. After 25 min, the dye front was no longer visible. On inspection, the buffer was warm to the touch, and the gel was hot. The gel was placed to stain. A new gel was cast, using the same conditions as above but with 30 ml gel, containing 1/10 of the Eosin (20 ppm). This gel also set in less than 10 min. It was loaded without preelectrophoresis and run at 50 V for 2 hrs. Possible bands were seen at 1 and 2 cm from the origin. The gel was stained in Coomassie Blue (Sigma) and destained in a mixture containing 40% "rubbing alcohol" (70% isopropanol) and 60% "distilled vinegar" (about 5% acetic acid).

A sample of the latter gel-forming mixture (20 ppm eosin) was exposed to daylight. It gelled in less than 1 min., at an ambient temperature of about 40 deg. Fahrenheit.

After two days of destaining, bands were seen in both the first and second submarine gels. In the first gel, after three days of destaining, at least 9 bands could be seen. Bands in the second gel were clearer, showing at least 10 bands (out of 13) across the central wells, in about the first centimeter of gel below the wells. The bands were sharp and easily discriminated.

Example 9

Vertical Gel.

A vertical gel was cast between glass plates with 0.5 mm spacers, using 6.4% Ac/Bis, 100 ppm DMPAP, 0.045 M TO buffer ("0.5×"), 0.1% SDS, 2000 ppm TEMED. Setting required between 5 and 10 min. in near UV The cassette leaked during the procedure, and was refilled by addition to the top while polymerizing; the leak was sealed, and a full cassette was polymerized. Proteins were loaded and run for 1.5 hr at 150 V, 24–30 mA. The gel was stained in Coomassie blue and destained; it destained to readability overnight. At least two bands were seen in the area below the wells. Patterns in the lower part of the gel were distorted, perhaps as a result of the difficulties of casting.

Lessons to be Learned From Examples 8 and 9 Include:
1. Gels of standard formats, both in cassettes and in "submarine" mode, can be made by use of the initiators and methods of the invention.
2. The technology appears to be suitable for industrial fabrication of gels for later use ("prefabricated gels"). In particular, the increase of light intensity from an inexpensive lamp to full daylight (ca. 1 W/ square meter) reduced polymerization time to less than 1 minute. Use of intense sources, such as Xenon lamps, lasers, or focussed sunlight, could reduce the gelation time to as little as one second. On the other hand, in dim interior illumination (but suitable for running gels, writing notes, etc.), prepared solutions with all ingredients needed for polymerization are stable for long periods—greater than a day, at least. Because successful polymerization was conducted in contact with plastic and rubber in Example 8, it will be possible to cast acrylic-type gels in contact with plastic support films, with exposure to the atmosphere. This is not feasible with conventional peroxygen-based techniques.
3. Because of the number of variables, and as in conventional methods for preparing gels for electrophoresis, a kit containing the appropriate amounts of the necessary ingredients will be useful to consumers. Because of the stability of these systems, it may be possible to prepare solutions which contain all the ingredients for electrophoresis, which are able to polymerize simply by illumination in the cassette, optionally after reconstitution with water.

What is claimed is:

1. An improved composition for the preparation by photopolymerization, in the presence of air at a light intensity of about 1000 mW/square centimeter or less, of gels for electrophoresis, wherein the composition comprises:
   a) an ethylenically unsaturated monomer, containing on average 1.0 or more units of ethylenic unsaturation;
   b) a crosslinking agent containing on average more than 1.0 units of ethylenic unsaturation, which may be the same as the monomer;
   c) a solvent, comprising 50% or more of the weight of the solution, and
   d) a photoinitiator system to polymerize the gel, in which the photoinitiator is not a riboflavin;

the improvement comprising selection of a photoinitiator and a concentration thereof which causes photopolymerization of the gel in about one minute or less in the presence of air at a light intensity of about 1000 mW/square centimeter or less.

2. A composition as in claim 1, in which the photoinitiator is selected from a phenone including an acetophenone or benzophenone, a fluorescein, a quinone, a hindered amine light stabilizer, a xanthone, a fluoroenone, an anthroquinone, an azobis nitrile, a derivative thereof, and a mixture thereof.

3. A composition as in claim 2, in which the initiator is selected from 2,2-dimethoxy-2-phenyl acetophenone and eosin.

4. A composition as in claim 1, in which at least 20% by weight of the monomer is selected from substantially non-ionic amides and esters of acrylic and methacrylic acids including acrylamide, ethylenically-unsaturated esters or ethers of substantially nonionic polymers, nonionic vinyl-amine compounds including N-vinyl pyrrolidone, and mixtures thereof.

5. A composition as in claim 1, in which the transfer agent comprises a nitrogen- or sulfur-containing molecule, which provides electron transfer from the photoinitiator to the ethylenically unsaturated monomer.

6. An improved method for preparing a gel for electrophoresis, the method comprising photopolymerizing, in the presence of air at a light intensity of about 1000 mW/square centimeter or less, a composition in a container, wherein the composition comprises:
 a) an ethylenically unsaturated monomer, containing on average 1.0 or more units of ethylenic unsaturation;
 b) a crosslinking agent containing on average more than 1.0 units of ethylenic unsaturation, which may be the same as the monomer;
 c) a photoinitiator system, in which the photoinitiator is not a riboflavin;
 d) and a buffered solvent, comprising 50% or more of the weight of the solution;
  the improvement comprising selection of a photoinitiator system which causes photopolymerization of the gel, in about one minute or less, at a light intensity of about 1000 mW/centimeter squared or less, in the presence of air.

7. A method according to claim 6, comprising selecting as the initiator a photoinitiator other than a riboflavin, the photoinitiator concentration being selected to cause the polymerization to a palpable gel of a mixture comprising 10% polyacrylamide and 0.5% methylenebisacrylamide in an alkaline buffered solution containing 100 ppm or more of tetramethylethylenediamine, in about one minute or less, at a light intensity of less than about 1000 mW/square centimeter, in a wavelength range functionally absorbable by the photoinitiator to initiate polymerization.

8. The method of claim 7 in which the initiator is an acetophenone, a benzophenone or a fluorescein, or a derivative thereof, including an eosin.

9. A gel for electrophoresis, prepared by polymerizing, photopolymerization in the presence of air at a light intensity of about 100 mW/square or less, a composition comprising:
 a) an ethylenically unsaturated monomer, containing on average 1.0 or more units of ethylenic unsaturation;
 b) a crosslinking agent containing on average more than 1.0 units of ethylenic unsaturation, which may be the same as the monomer;
 c) a solvent, comprising 50% or more of the weight of the solution, wherein the solvent is buffered; and
 d) a photoinitiator system
  wherein the photoinitiator system causes photopolymerization of the gel in about one minute or less in the presence of air at a light intensity of about 1000 mW/centimeter squared, or less.

10. A gel as in claim 9, wherein the gel is formed by photopolymerization while at least about 20% of the surface area of said gel is exposed to air.

11. A gel as in claim 10, wherein at least 30% of the surface area of the gel is exposed to air during polymerization.

12. A gel as in claim 9, wherein the gel is formed by photopolymerization in the presence of shape-forming constraints which are substantially formed of plastic.

13. A gel as in claim 9, further comprising a gradient of gel concentration or of crosslink density, said gradient formed by using as an initiator of gel formation a photoinitiator other than a riboflavin, and imposing a gradient of exposure to light during the polymerization of the gel, the light having a wavelength of 200 to 1500 nanometers, and wherein the gel will polymerize when at least 20% of the surface of said gel is exposed to air during polymerization.

14. A gradient gel as in claim 13, wherein the gradient is either horizontal or vertical with respect to the electric field.

15. A gel according to claim 9, wherein the gel is cast in contact with at least one sheet of support material.

16. A gel as in claim 9, wherein the gel contains denaturing agents for the sequencing of a nucleic acid.

17. A gel as in claim 9, wherein the gel contains denaturing agents for the separation of SDS-denatured proteins.

18. A gel as in claim 9, wherein the buffer permits the analysis of non-denatured proteins.

19. An improved composition as in claim 1, further characterized in that the improvement comprising use of a photoinitiator system to polymerize the gel, the photoinitiator system comprising a photoinitiator and optionally transfer agents, in which the photoinitiator is selected from an acetophenone di- or tri-substituted at the 2 position, an acetophenone substituted at the 3, 4 and/or 4' position, a xanthophenone substituted at the 2, 3, 4, and/or 4" position, benzoin and its lower alkyl derivatives, and fluorescein and derivatives thereof.

* * * * *